US 6,719,710 B2

United States Patent
Darcey

(10) Patent No.: US 6,719,710 B2
(45) Date of Patent: *Apr. 13, 2004

(54) ROLL FORM MEDICAL BANDAGING PRODUCT, MEDICAL BANDAGE MATERIAL, METHOD OF CONSTRUCTING SAME, AND BANDAGING METHOD

(75) Inventor: Thomas D. Darcey, Mooresville, NC (US)

(73) Assignee: BSN Medical, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/760,032

(22) Filed: Jan. 12, 2001

(65) Prior Publication Data

US 2002/0133107 A1 Sep. 19, 2002

(51) Int. Cl.⁷ .................................................. A61F 5/00
(52) U.S. Cl. ..................................... 602/8; 602/5; 602/6
(58) Field of Search .............................. 602/5, 6, 7, 8, 602/10, 11, 41, 46

(56) References Cited

U.S. PATENT DOCUMENTS

| | | | | |
|---|---|---|---|---|
| 4,770,299 A | * | 9/1988 | Parker | 206/389 |
| 4,869,046 A | | 9/1989 | Parker | |
| 4,899,738 A | | 2/1990 | Parker | |
| 5,003,970 A | | 4/1991 | Parker et al. | |
| 5,480,376 A | * | 1/1996 | Duback et al. | 602/8 |
| 5,607,387 A | | 3/1997 | Martin et al. | |
| 5,755,678 A | * | 5/1998 | Parker et al. | 602/6 |
| 6,231,533 B1 | * | 5/2001 | Novich et al. | 602/5 |
| 6,290,663 B1 | * | 9/2001 | Darcey | 602/5 |

FOREIGN PATENT DOCUMENTS

GB 2068237 A * 8/1981 ............ A61F/5/04

OTHER PUBLICATIONS

Delta–Splint Synthetic Roll; Instructions for Use and Product Description; DePuy, a Johnson & Johnson Company; Massachusetts, USA.

OCL PolyLITE synthetic splinting system; Instructions for use and Product Description; M–PACT Worldwide, Inc.; Eudora, Kansas, USA.

\* cited by examiner

Primary Examiner—Danton D. DeMille
Assistant Examiner—Quang D. Thanh
(74) Attorney, Agent, or Firm—Adams Evans P.A.

(57) ABSTRACT

A medical bandaging product in roll form for being dispensed in predetermined lengths suitable for a given medical use, and including an elongate sleeve formed of moisture-impervious material and sealable to prevent entry of moisture, and an elongate medical bandage material substantially the same length as the sleeve and positioned in the sleeve in a single length along the length of the sleeve and sealed therein against entry of moisture until use. The medical bandage material includes a substrate and a reactive system impregnated into or coated onto the substrate. The system remains stable when maintained in substantially moisture-free conditions and hardens upon exposure to sufficient moisture to form a rigid, self supporting structure. A protective liner sheet encloses the substrate along its length and forms a barrier between the substrate and the sleeve during storage, and is optionally removable after removal of the medical bandage material from the sleeve and prior to application to a patient. The substrate is adapted for having a protective padding material interposed between the substrate and the patient.

8 Claims, 10 Drawing Sheets

ROLL FORM MEDICAL BANDAGING PRODUCT, MEDICAL BANDAGE MATERIAL, METHOD OF CONSTRUCTING SAME, AND BANDAGING METHOD

TECHNICAL FIELD AND BACKGROUND OF THE INVENTION

The present invention relates generally to the field of orthopedic medicine and more specifically to the design of an improved medical bandaging product and material formed of a moisture-curable plastic material, a method for constructing such an improved medical bandage, and a method of constructing and applying an improved bandaging product.

Medical bandages for use in the treatment of injuries, such as broken bones requiring immobilization of a body member, are generally formed from a strip of fabric or scrim material impregnated with a substance which hardens into a rigid structure after the strip has been wrapped around the body member. The hardening substance traditionally used in carrying out this procedure is plaster-of-paris.

Conventional practice has been to fabricate a cast or splint upon an injured limb by initially applying to the limb a protective covering of a cotton fabric or the like and then overwrapping the covering and limb with a woven cloth impregnated with plaster-of-paris which has been wetted by dipping in water immediately prior to application. This practice is still in widespread use but possesses several significant disadvantages. For example, the above-described application procedure is messy and time consuming. Several components are required and considerable skill is necessary.

In order to alleviate the above-recited disadvantages of the conventional application procedure for plaster-of-paris casts and splints, unitary splinting materials have been devised and are disclosed in, for example, U.S. Pat. Nos. 3,900,024, 3,923,049, and 4,235,228. All of these patents describe a padding material with a plurality of layers of plaster-of-paris impregnated cloth. Such unitary splinting materials are not as messy and can be applied more quickly but still suffer from a number of disadvantages inherent in plaster-of-paris cast materials. All plaster-of-paris splints have a relatively low strength to weight ratio which results in a finished splint which is very heavy and bulky. Plaster-of-paris splints are slow to harden, requiring 24 to 72 hours to reach maximum strength. Since plaster-of-paris breaks down in water, bathing and showering are difficult. Even if wetting due to these causes can be avoided, perspiration over an extended period of time can break down the plaster-of-paris and create a significant problem with odor and itching.

A significant advance in the art of casting and splinting is disclosed in U.S. Pat. Nos. 4,411,262 and 4,502,479. The casting materials disclosed in these patents comprise a flexible fabric impregnated with a moisture-curing resin enclosed in a moisture-free, moisture-impervious package. Compared to plaster-of-paris, these products are extremely lightweight, have a very high strength to weight ratio and can be made relatively porous, permitting a flow of air through the casting material. Prior art moisture-curing systems include a package within which is contained a plurality of layers of fabric, such as fiberglass, impregnated with a moisture-curing resin. No provision is made for reclosing the package, so that the entire material must be very quickly used after removal from the package since such moisture-curing resins will cure in a relatively short period of time due merely to contact with atmospheric moisture.

U.S. Pat. Nos. 4,770,299 and 5,003,970, among others owned by applicant, each disclose roll-form synthetic bandaging products which include the ability to dispense desired lengths of bandaging material when needed, while sealing the remaining length of material for later use. These products have proven to be very successful in many applications, since they include a padding material on both sides, thereby permitting quick and easy application. Similar products are also sold in precut lengths sealed in a single use, moisture impervious envelope.

From the above discussion, it can be seen that both the conventional plaster-of-paris casting method and the more recent moisture-curable resin casting method possess both advantages and disadvantages. On the one hand, plaster-of-paris casts are bulky, heavy and difficult to apply whereas moisture-curable resin casts are lightweight, durable and relatively easy to apply. Plaster-of-paris can be very easily stored and used as needed since it has a relatively long shelf life so long as it is not completely wetted. On the other hand, the moisture-curable resins are very sensitive to the presence of even minute amounts of moisture which requires that either the materials be packaged in a wide variety of different shapes and sizes or unused portions be discarded, generating a substantial amount of waste and increasing the effective cost of the product.

Current padded, synthetic roll-form products are, however, relatively expensive and limit the option of the physician to use less padding or padding in different densities or thicknesses from one point on the splint to another.

This invention combines the advantages of both plaster-of-paris and moisture-curable resin systems while avoiding their respective disadvantages. This is accomplished by providing a unitary splinting system with improved strength and convenience. A unitary system is provided with the use of moisture-curing resin casting materials, together with a moisture-impervious package with means for resealing the package against entry of moisture after a desired length of bandaging product has been removed for use. In this manner, hardening of the bandaging product remaining in the moisture-impervious package is prevented thereby increasing the cost effectiveness of the system substantially. The product provides enhanced flexibility of use and reduced cost in comparison with other synthetic cast products by omitting the padding from the product, which may be then added by the technician during application of the splint or bandage.

SUMMARY OF THE INVENTION

It is therefore an object of the invention to provide an unpadded medical bandaging product in roll form with a moisture-curable resin which hardens the material upon exposure to moisture to form a rigid, self-supporting structure.

It is another object of the invention to provide an unpadded medical bandaging product which can be dispensed in any desired length while preventing hardening of the remaining material until use is desired.

It is another object of the invention to provide a unitary, unpadded medical bandaging product which includes a liner which can either be left on the substrate of the product or removed prior to application to the patient.

It is another object of the invention to provide a medical bandaging product which is less expensive that similar products with preapplied padding.

It is another object of the invention to provide a medical bandaging product which permits the technician applying the bandage to custom-apply and fit the padding to the substrate during application.

It is another object of the invention to provide a method of constructing a medical bandaging product which permits a wide variety of padding applications determined at the point of treatment.

These and other objects and advantages of the present invention are achieved in the preferred embodiment disclosed below by providing a medical bandaging product in roll form for being dispensed in predetermined lengths suitable for a given medical use, and comprising an elongate sleeve formed of moisture-impervious material and sealable to prevent entry of moisture, and an elongate medical bandage material substantially the same length as the sleeve and positioned in the sleeve in a single length along the length of the sleeve and sealed therein against entry of moisture until use. The medical bandage material comprises a substrate and a reactive system impregnated into or coated onto the substrate. The system remains stable when maintained in substantially moisture-free conditions and hardens upon exposure to sufficient moisture to form a rigid, self supporting structure. A protective liner sheet encloses the substrate along its length and forms a barrier between the substrate and the sleeve during storage, and is optionally removable after removal of the medical bandage material from the sleeve and prior to application to a patient. The substrate is adapted for having a protective padding material interposed between the substrate and the patient. Resealing means is provided for resealing the sleeve against entry of moisture after a predetermined length of the bandaging product has been dispensed for use to prevent hardening of the substrate remaining in the sleeve.

According to one preferred embodiment of the invention, the sleeve comprises an aluminum foil laminate having an outer tear resistant layer, a central aluminum foil layer and an inner heat sealable plastic layer.

According to another preferred embodiment of the invention, the substrate comprises a plurality of knitted or woven fabric layers.

According to yet another preferred embodiment of the invention, the protective liner sheet enclosing the substrate comprises a fibrous nonwoven material.

According to yet another preferred embodiment of the invention, the protective liner sheet enclosing the substrate comprises a nonwoven polypropylene sheet folded along its longitudinal axis to define an envelope within which the substrate is positioned.

According to yet another preferred embodiment of the invention, the reactive system comprises a blended polyisocyanate, polyol, catalyst and stabilizer.

According to yet another preferred embodiment of the invention, the resealing means for resealing the sleeve is selected from the group consisting of tape, a clamp, a clip for holding a folded end of the sleeve closed and a restricted opening through which the sleeve is extended.

According to yet another preferred embodiment of the invention, the roll comprises the sleeve with the medical bandage material therein and the sleeve formed into a coil.

Preferably, the invention includes a dispenser within which the coil of bandaging material is contained.

According to yet another preferred embodiment of the invention, the dispenser comprises a container within which the roll is positioned, the container defining a slot therein in which the leading end of the coil may be positioned and through which the product is dispensed as needed.

According to yet another preferred embodiment of the invention, a medical bandaging product is provided for being packaged in predetermined lengths suitable for a given medical use, and comprises a sleeve formed of moisture-impervious material and sealable to prevent entry of moisture and a medical bandage material positioned in the sleeve and sealed therein against entry of moisture until use. The medical bandage material comprises a substrate, a reactive system impregnated into or coated onto the substrate, the system remaining stable when maintained in substantially moisture-free conditions and hardening upon exposure to sufficient moisture to form a rigid, self supporting structure. A protective liner sheet encloses the substrate and forms a barrier between the substrate and the sleeve during storage and is optionally removable after removal of the medical bandage material from the sleeve and prior to application to a patient. The substrate is adapted for having a protective padding material interposed between the substrate and the patient.

According to yet another preferred embodiment of the invention, a medical bandaging product having a predetermined length suitable for a given medical use is provided, and comprises an enclosure formed of a moisture-impervious material sealable to prevent entry of moisture. The enclosure includes an elongate, resealable dispensing sleeve with a medical bandage material positioned in the enclosure and sealed therein against entry of moisture until use. The medical bandage material comprises a substrate formed of a plurality of knitted or woven fabric layers, a reactive system impregnated into or coated onto the substrate, the system remaining stable when maintained in substantially moisture-free conditions and hardening upon exposure to sufficient moisture to form a rigid, self supporting structure and comprising a blended polyisocyanate, polyol, catalyst and stabilizer. A soft, flexible protective nonwoven liner sheet encloses the substrate along its length and provides a barrier between the substrate and the sleeve within which the medical bandage material is enclosed. The liner sheet is adapted for being removed from the substrate after removal from the sleeve and prior to application to the patient. The medical bandage material is positioned in the enclosure for being dispensed in a desired use length from the sleeve. The sleeve is adapted for being resealed to prevent moisture from entering the enclosure.

An embodiment of the method of constructing a medical bandaging product according to the invention comprises the steps of providing an elongate, moisture-impervious sleeve and an elongate medical bandage material comprised of a substrate enclosed within a protective liner sheet, impregnating into or coating onto the substrate a reactive system which remains stable when maintained in substantially moisture-free conditions and hardens upon exposure to sufficient moisture to form a rigid, self-supporting structure, and positioning a length of the elongate medical bandage material within the elongate sleeve which is generally the same length as the sleeve and which extends along the length of the sleeve in a single layer. The sleeve is sealed to prevent entry of moisture until use.

According to one preferred embodiment of the method of the invention, the steps include providing a moisture impervious sleeve and a substrate for being enclosed within a protective liner sheet, and impregnating into or coating onto the substrate a reactive system which remains stable when maintained in substantially moisture-free conditions and hardens upon exposure to sufficient moisture to form a rigid, self-supporting structure. The coated or impregnated substrate is positioned within the protective liner sheet to form a medical bandage material. A length of the elongate medical bandage material is positioned within the elongate sleeve. The medical bandage material is generally the same length as the sleeve and extends along the length of the sleeve in a single layer. The sleeve is sealed to prevent entry of moisture until use.

According to one preferred embodiment of the invention, the method includes the step of rolling the elongate sleeve with the medical bandage material therein into a coil.

According to another preferred embodiment of the invention, the method includes the step of packaging the coil in a dispenser.

According to yet another preferred embodiment of the invention, the dispenser comprises a box provided with a slot therein for feeding a desired length of the sleeve therethrough.

A further embodiment of the method according to the invention comprises a method of utilizing a medical bandaging product, comprising the steps of providing an elongate sleeve and an elongate medical bandage material comprised of a substrate enclosed within a protective liner sheet, impregnating into or coating onto the substrate a reactive system which remains stable when maintained in substantially moisture-free conditions and hardens upon exposure to sufficient moisture to form a rigid, self-supporting structure, positioning the elongate medical bandage material within the elongate sleeve, and sealing the sleeve to prevent entry of moisture until use. The medical bandage material is removed from the sleeve immediately prior to use. The liner sheet is optionally removed from the substrate, and the substrate is wetted to activate the reactive system. A padding is interposed between the substrate and the patient. The substrate and interposed padding is applied to the patient.

According to one preferred embodiment of the invention, the step of interposing the padding between the patient and the substrate includes the step of applying the padding to the patient before the substrate is applied to the patient.

According to another preferred embodiment of the invention, the step of interposing the padding between the patient and the substrate includes the step of applying the padding to the substrate before application to the patient.

According to another preferred embodiment of the invention, the method includes the step of overwrapping the padding and substrate with an elastic bandage to maintain the padding and substrate in close conformity with the patient during curing of the moisture-curable resin.

BRIEF DESCRIPTION OF THE DRAWINGS

Some of the objects of the invention have been set forth above. Other objects and advantages of the invention will appear as the description of the invention proceeds when taken in conjunction with the following drawings, in which.

DESCRIPTION OF THE PREFERRED EMBODIMENT

Figure 1:
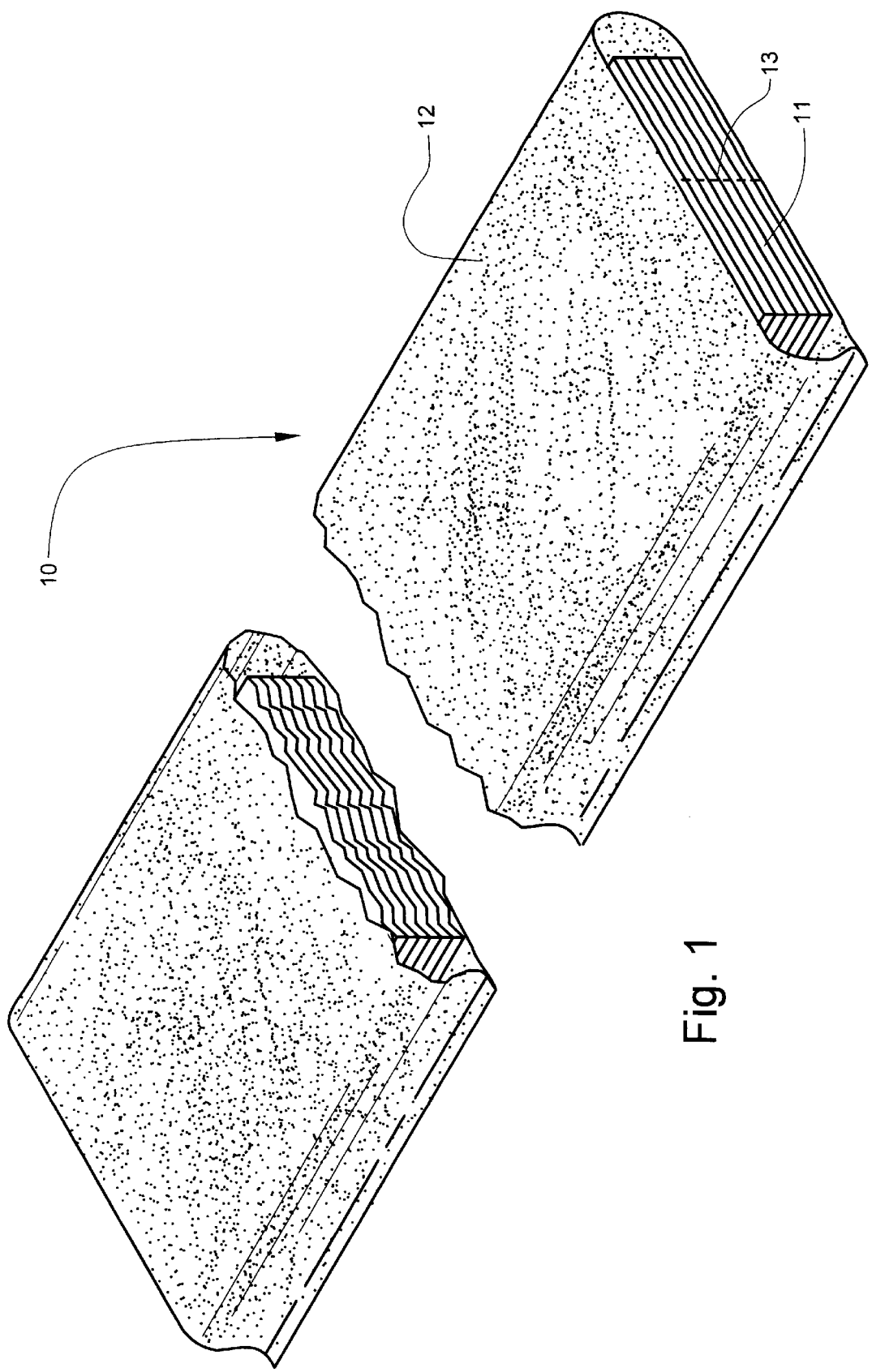
FIG. 1 is a perspective view of a length of medical bandage material according to one preferred embodiment of the invention.

Referring now specifically to the drawings, a medical bandaging material according to the present invention is shown generally in FIG. 1 at 10. The medical bandaging material 10 includes a substrate 11 loosely and removably enclosed within a thin liner sheet 12. As is more specifically shown in FIGS. 2, 3 and 4, the substrate 11 preferably comprises 7 layers of woven or knitted fabric 11a–11g overlaid in registration with each other. The preferred substrate material is the fiberglass substrate material used by applicant in its Orthoglass padded splint material. Any suitable widths may be constructed, but conventional widths are presently one to six inches, in one-inch increments.

Other substrate materials may be used, including a core formed of first and second fiberglass fabric sheets with a laminated low density core sandwiched between the fiberglass sheets.

Other fabrics which may be suitable for the sheets include fabrics made of a composition of aluminum oxide, silicone oxide and boron oxide and sold under the trademark Nextel 440 by Thermostatic Industries, Inc.; silica-based fabrics, and high modulus fabrics sold under the DuPont trademark "Kevlar."

A suitable low density core is a single thickness sheet of random laid non-continuous polyester nonwoven fabric incorporating a styrene-soluble binder filled 60 percent by volume with plastic microspheres. The product is sold under the trademark "Firet Coremate XM" manufactured by Baltek. This product is available in 2 mm, 3 mm and 4 mm thicknesses. The 2 mm thickness has been found suitable, and weighs 2.7–3.2 oz/yd$^2$, has a cured specific gravity of 31.0–37.0 lb/ft$^3$, and a resin consumption of 3.1–3.3 oz/ft$^3$.

Other Firet Coremat grades, such as Firet Coremat XX and Firet Coremat XW may also be suitable. These grades are filled with plastic microspheres to 50 percent by volume. Other products which may be suitable include a low density, nonwoven continuous strand fabric such as BaltekMat T-2000. This product has characteristics which are generally similar to Firet Coremat, but is generally unavailable in small quantities.

Figure 2:
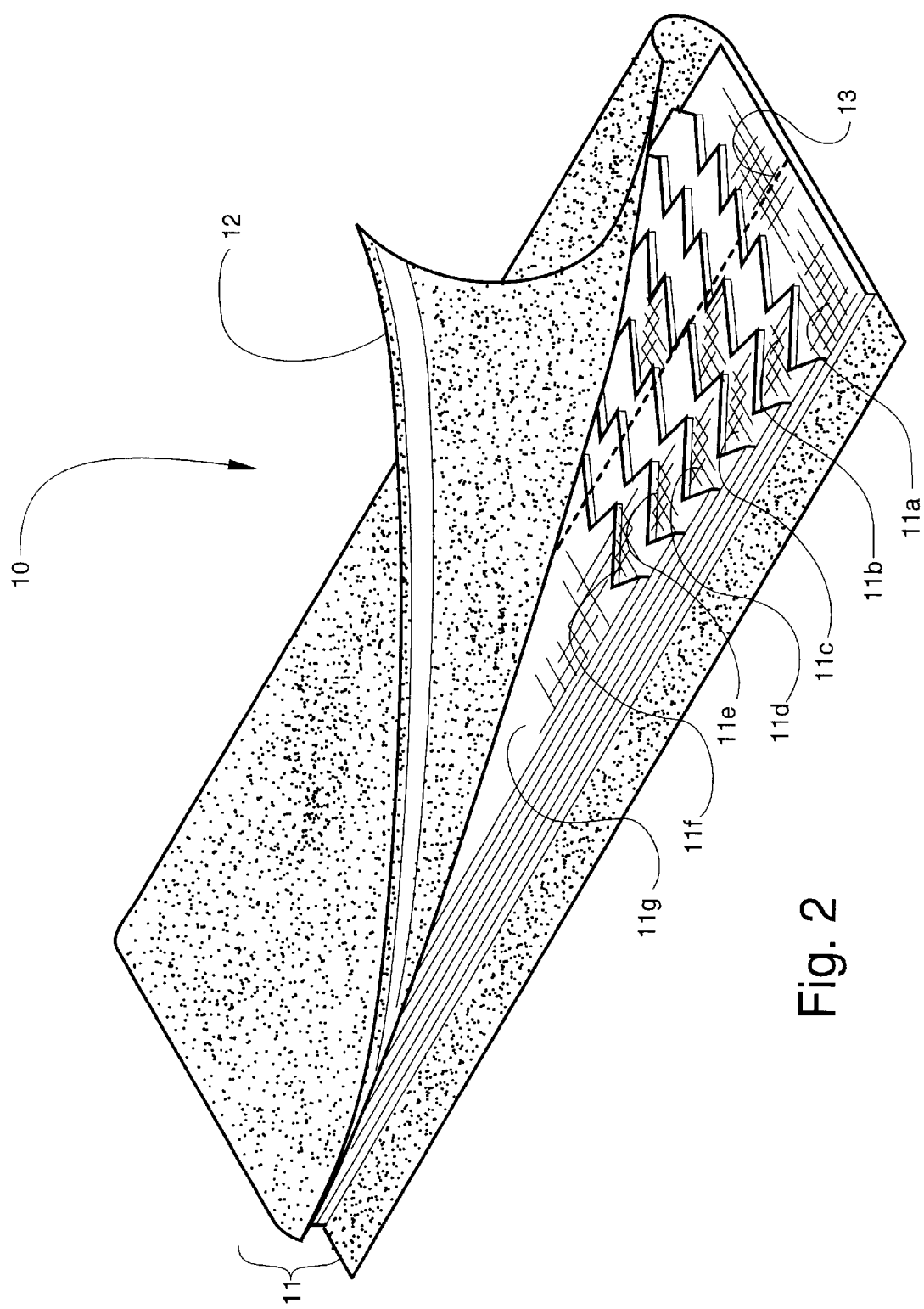
FIG. 2 is a fragmentary perspective view of the embodiment shown in FIG. 1.

As is shown in FIG. 2, the fiberglass woven or knitted fabric sheets 11a–11g are integrated and maintained in registration with each other by sewing stitches 13 which extend down the center of the substrate along its longitudinal axis.

Substrate 11 is impregnated or coated with a reactive system which remains stable when maintained in substantially moisture-free conditions but which hardens upon exposure to sufficient moisture to form a rigid, self-supporting structure. A typical formulation of the reaction system is set forth in the following table:

| Typical Formulation: | | |
|---|---|---|
| Isonate↓ 143L or Mondur↓ CD or Rubinate↓ X1168 | polyisocyanate | 50.0% |
| Pluracol↓ P1010 | polyol | 46.6% |
| DC-200 Silicone | defoaming agent | 0.30% |
| Benzoyl Chloride | stabilizer | 0.10% |
| Thancat↓ DM-70 | catalyst | 3.0% |
| | | 100% |

A complete discussion of the parameters of the reactive system, the manner of production and the variables which apply are found in U.S. Pat. No. 4,411,262, referred to above.

Figures 3, 4:
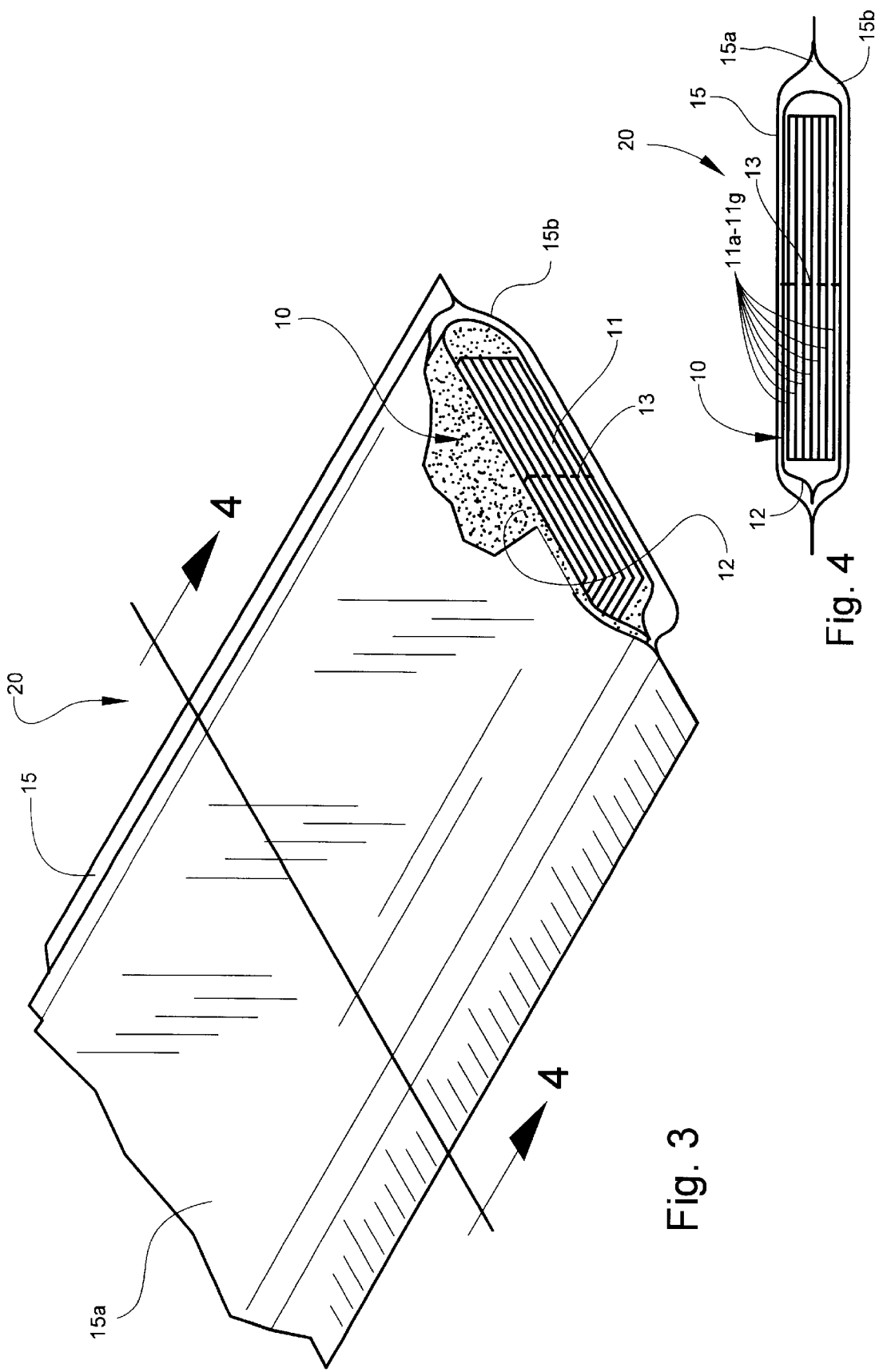
FIG. 3 is a fragmentary perspective view of the medical bandaging product according to a preferred embodiment of the invention.
FIG. 4 is a cross-sectional view taken along lines 4—4 of FIG. 3.

The liner sheet 12 is preferably a low density, thin non-woven material with just enough thickness and density to retain the resin on the substrate 11 and away from the inner surface of the sleeve 15. One such suitable product is a white polypropylene nonwoven material constructed of 4 denier continuous filament fiber having a weight of 1 oz/yd.$^2$ (31 g./m$^2$). The liner sheet 12 is preferably 13.5 mils (0.34 mm) thick. The liner sheet 12 is folded in half along its longitudinal axis to form an envelope, and the substrate 11 is enclosed within the folded sheet 12. This is shown in FIGS. 1, 2 and 4. The liner sheet extends out from one side of the substrate 11 and is closed by a length of tape 14 which extends longitudinally along the length of the bandaging material 10.

The liner 12 also provides a slick, low-friction contact surface with the inner surface of the sleeve 15.

As is also shown in FIGS. 3 and 4, the medical bandaging material 10 is packaged in moisture-free conditions in a foil sleeve 15, which is formed of two laminated elongate foil sheets 15a, 15b, placed in registration and heat sealed along their opposite sides to form a tube. The medical bandaging material 10 in the foil sleeve forms a medical bandaging product 20.

The outer layer of the laminate is formed of a tear-resistant plastic film. The middle layer comprises aluminum foil and acts as a moisture barrier. The inner layer is a plastic film having thermoplastic properties suitable for heat sealing the interior of sleeve 15 securely against moisture intrusion. This sleeve 15 is currently used by applicant as the moisture impervious enclosure of its Orthoglass splinting product.

Figure 5:
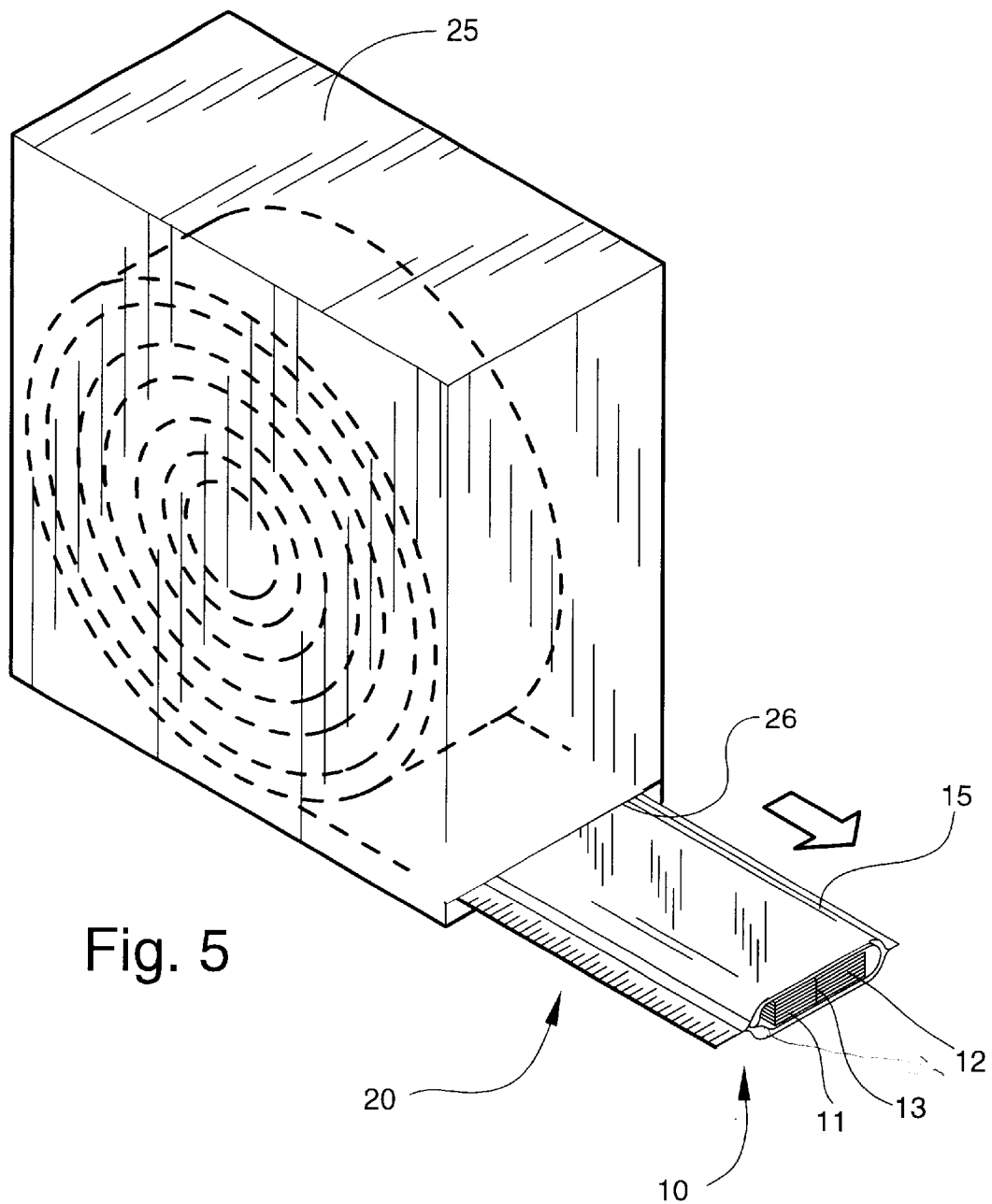
FIG. 5 is a perspective view of the medical bandaging product, including an embodiment of the dispensing box.
Figure 6:
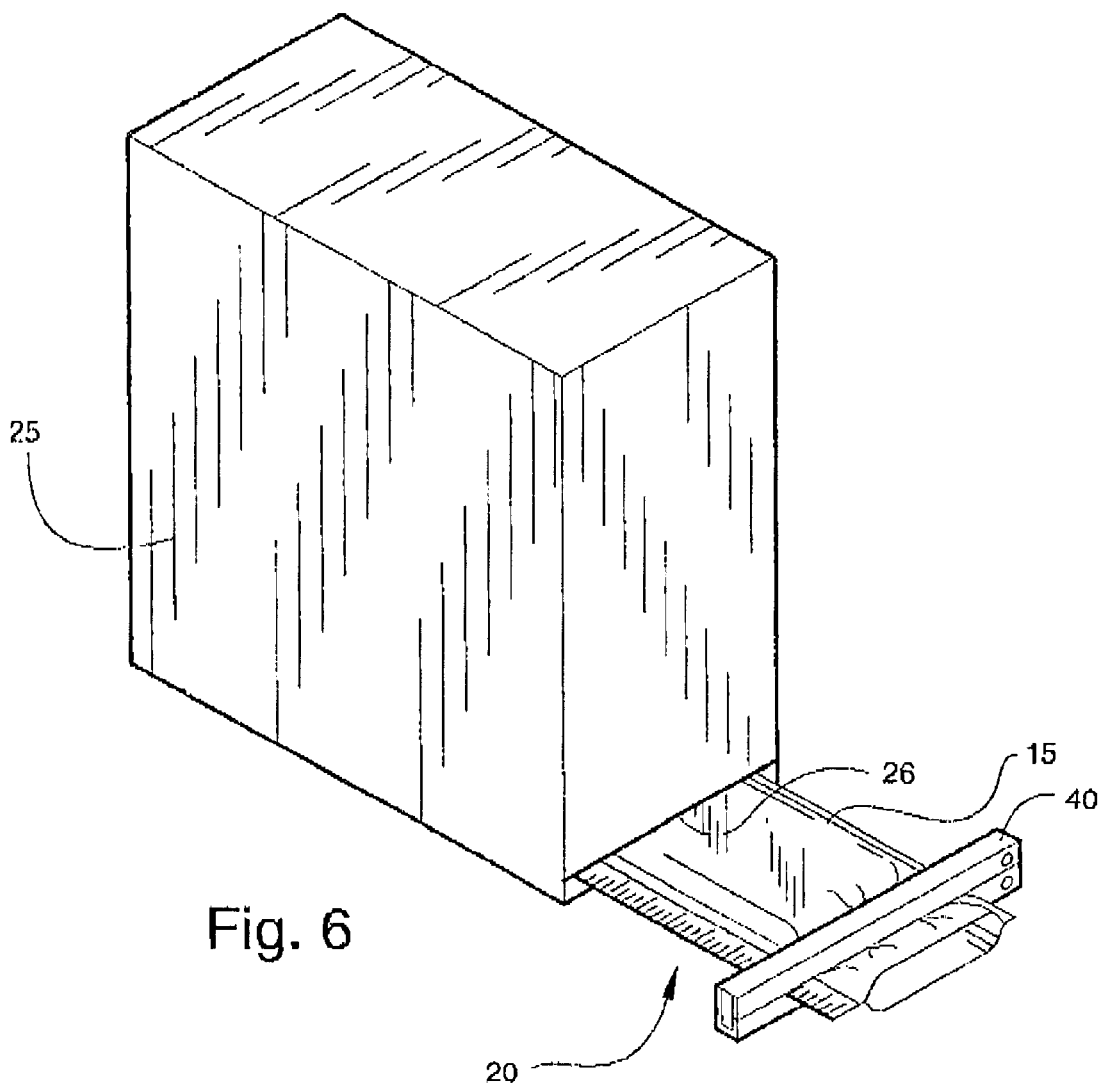
FIG. 6 is a perspective view of the medical bandaging product shown in FIG. 5, showing the manner of closing the foil sleeve after use.

Bandaging material product 20 may be sold in any convenient length, such as 24 feet, and is rolled into a coil and positioned in a suitable dispensing box 25, as is shown in FIGS. 5 and 6. Dispensing box 25 is provided with a slot 26 at one lower corner through which bandaging product 20 extends.

Referring now to FIGS. 7–10, an alternative medical bandaging product 30 is shown, and comprises a moisture-impervious foil bag 31 within which is contained a desired length of coiled medical bandaging material 10 as described above. The foil bag 31 is constructed of the same laminated foil material described above, and includes an enlarged enclosure 34 within which the medical bandaging material 10 is contained, and an elongate dispensing sleeve 36 having an open end 37 through which the end of the medical bandaging material 10 is extended for dispensing.

Figure 7:
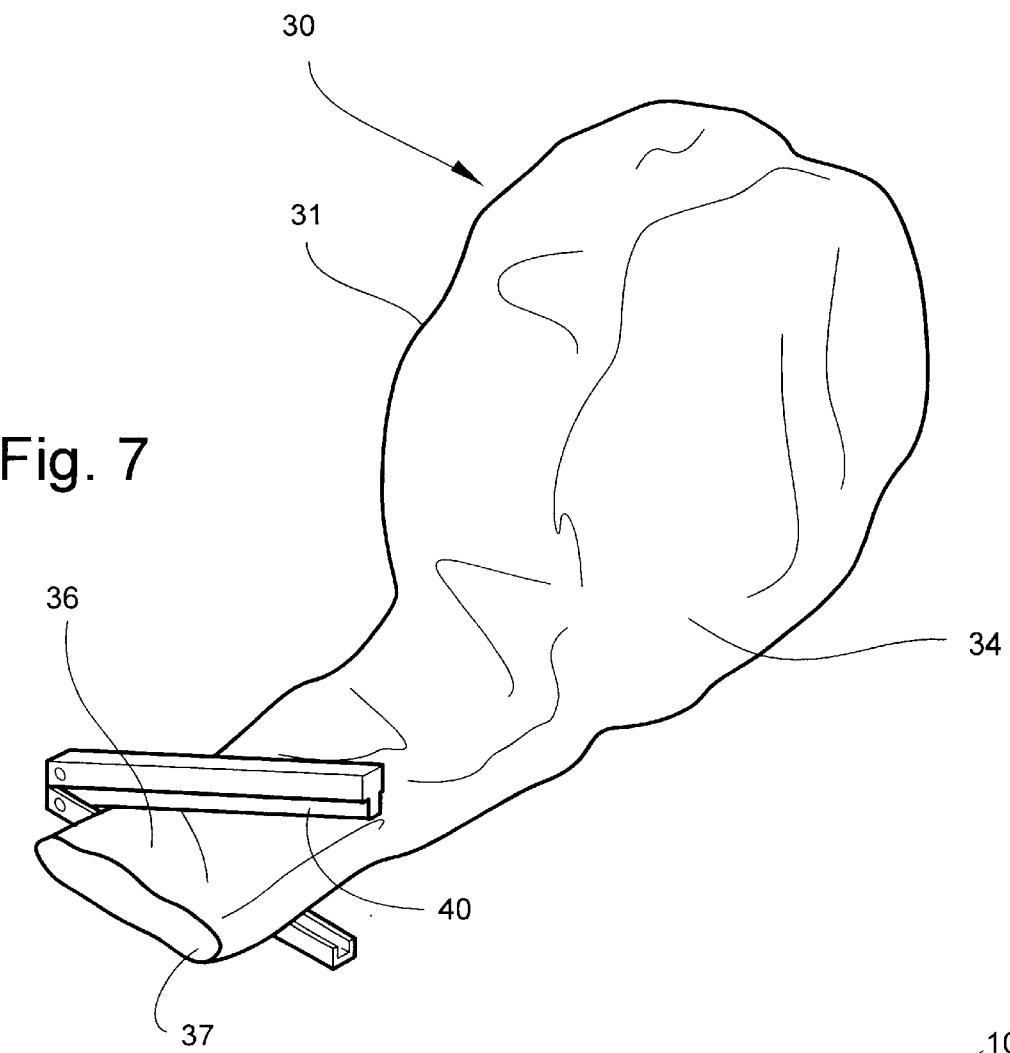
FIG. 7 is a perspective view of an embodiment of the medical bandaging product including an alternative moisture-impervious foil bag with an elongate dispensing sleeve.
Figure 8:
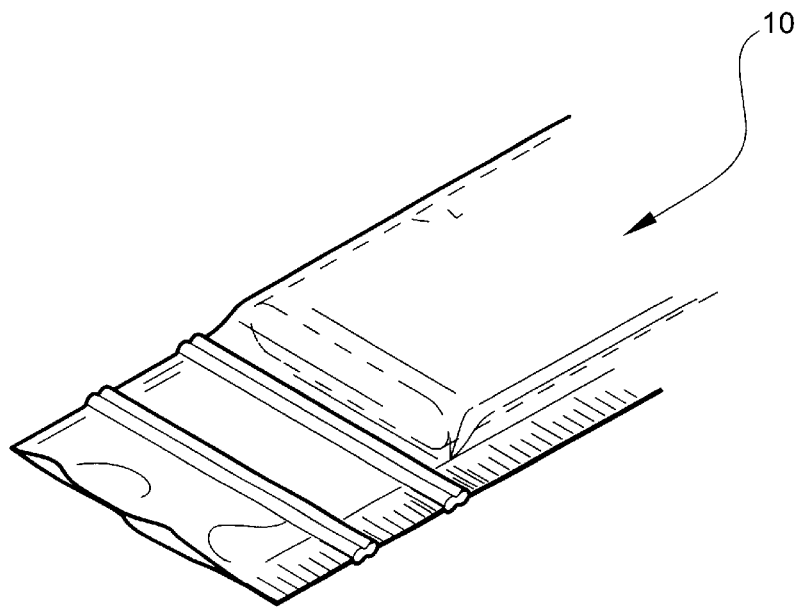
FIG. 8 is a fragmentary perspective view of one embodiment of the medical bandaging product with a zip end closure.
Figure 9:
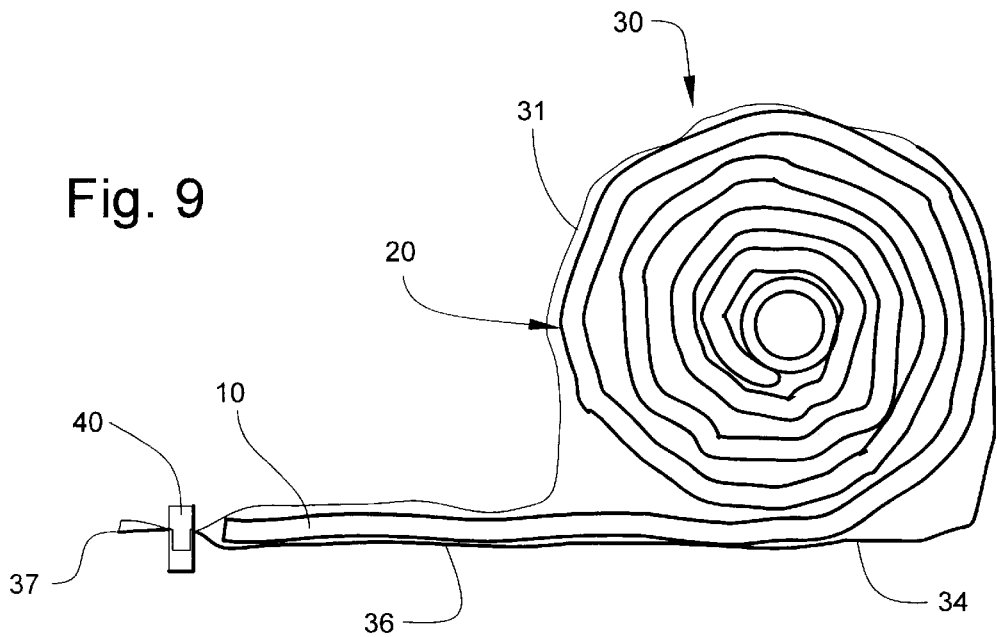
FIG. 9 is a vertical cross section of the foil bag shown in FIG. 7.
Figure 10:
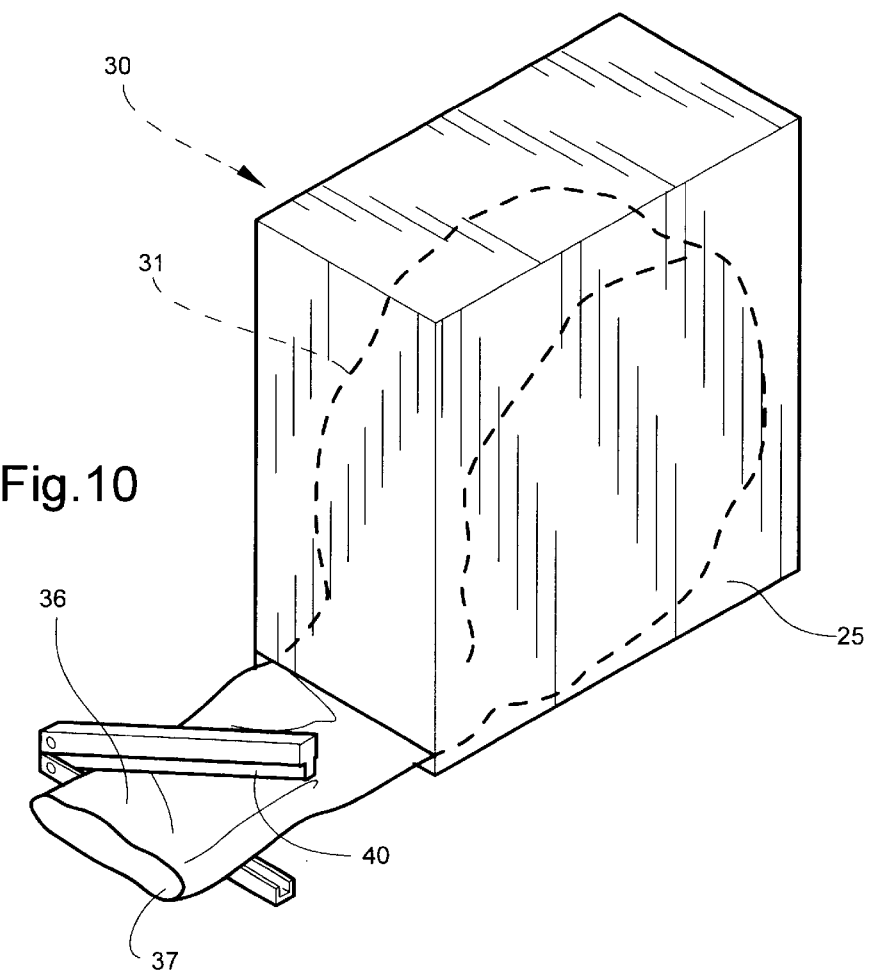
FIG. 10 is a perspective view of the foil bag shown in FIGS. 7 and 8 in a dispensing box, and showing a preferred manner of resealing the dispensing sleeve.
Figure 11:
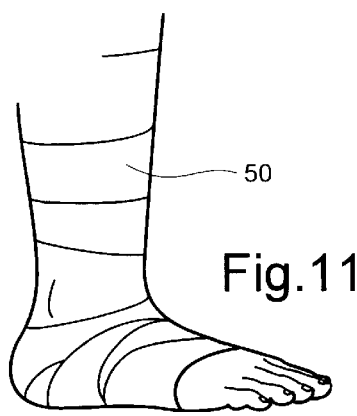
FIGS. 11–19 illustrate a preferred manner of preparing and applying the medical bandage material according to the invention.
Figure 12:
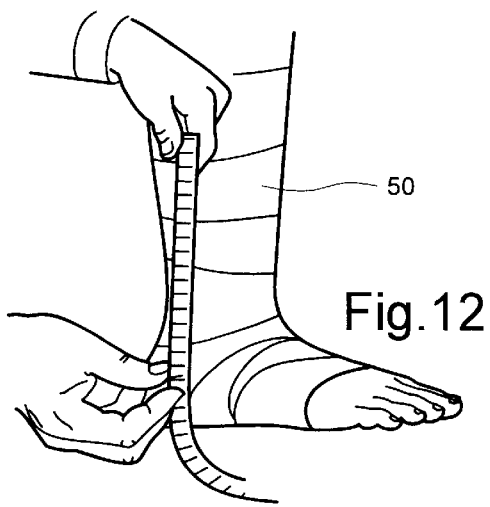
Figure 13:
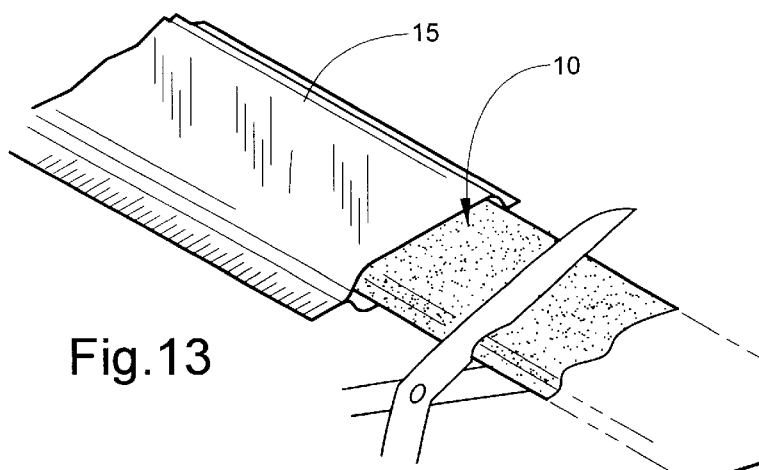
Figure 14:
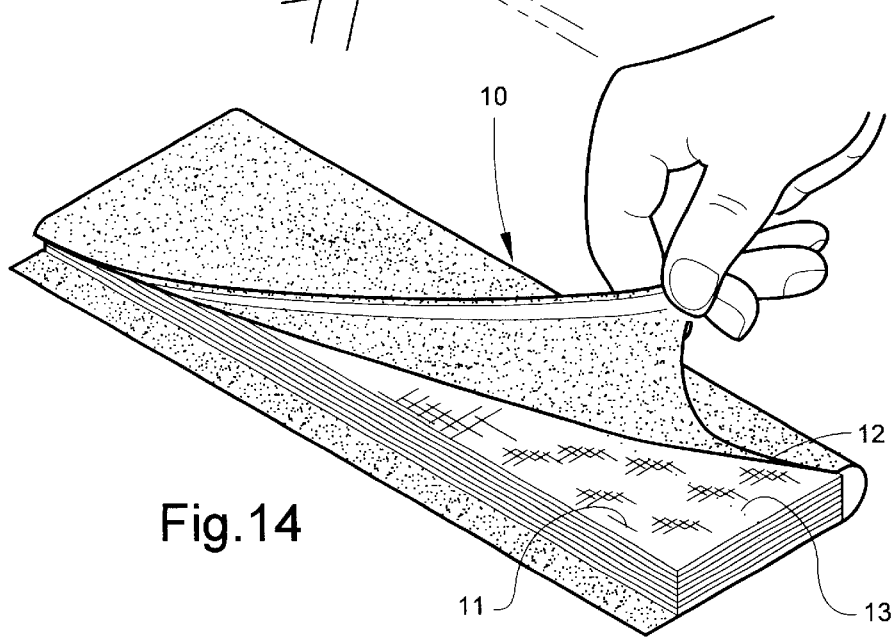
Figure 15:
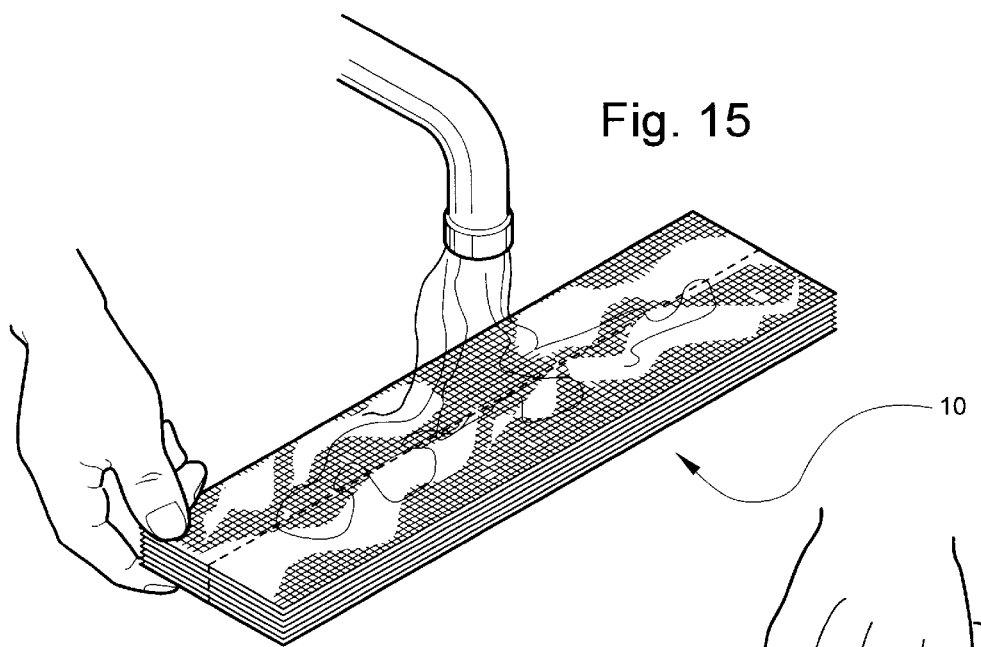
Figure 16:
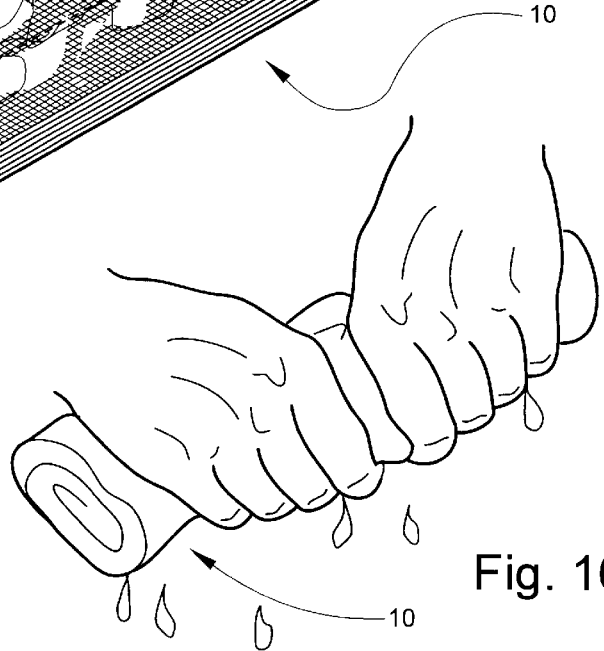
Figure 17:
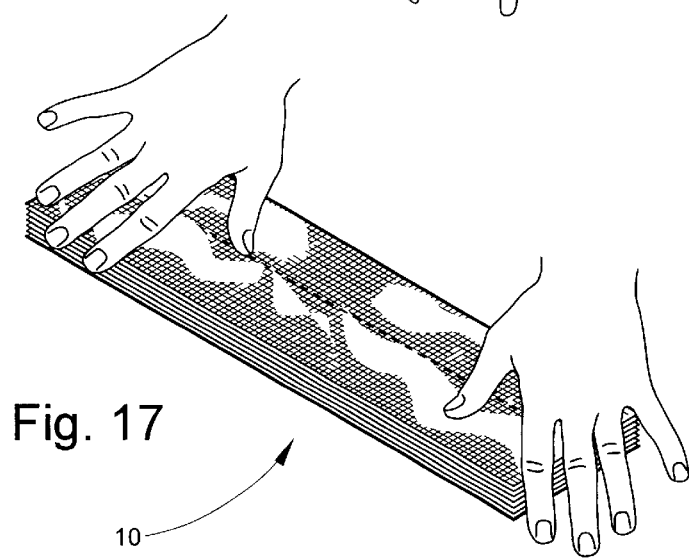
Figure 18:
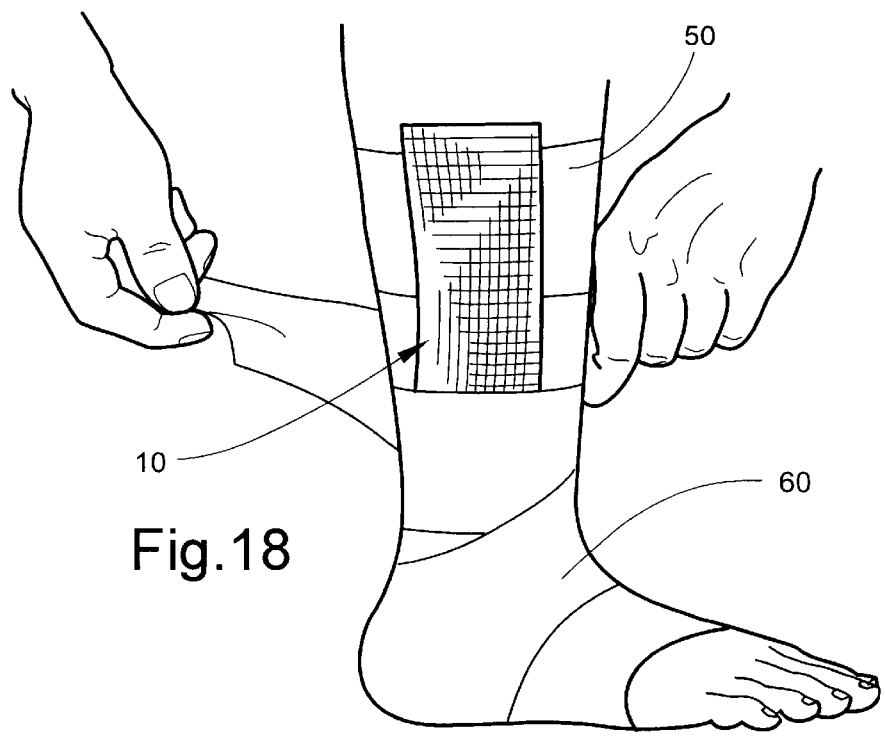
Figure 19:
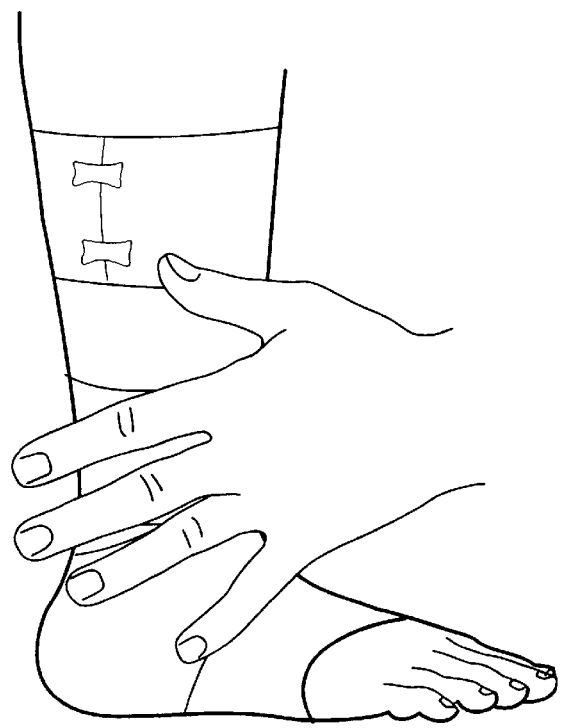

As is best shown in FIGS. 7 and 10, the end of sleeve 36 is sealed with sealing means, such as a clamp 40. Tape, a clip for holding a folded end of the sleeve closed, a zip-type closure (see FIG. 8) or other closure means may be used. The sleeve 36 should relatively snugly surround the medical bandaging material 10 so as to retard entry of moisture into the bag 30 during dispensing.

Other types of sealing mechanisms are possible such as, for example, a soft, conformable gasketing device with spring loaded compression, leverage clamping or screw action of sufficient strength to prevent entry of moisture into sleeve 15 or 36. Another suitable device is a pair of spring loaded rollers which, as compression takes place rolls slightly backwards, pushing medical bandage material 10 back slightly into sleeve 15 or 36 to permit a better seal.

Another possible sealing means shown) is a device which pushes the medical bandage material 10 back into the sleeve 15 or 36 a sufficient distance (approximately one inch), so that the open end may be heat sealed.

Referring now to FIGS. 11–20, preparation and application of the medical bandaging material 10 is illustrated.

Because the medical bandaging material 10 does not include padding, plastic gloves must be worn.

The injured extremity is first wrapped with an appropriate thickness of a padding material 50. Different thicknesses of padding 50 can be used on different parts of the injured limb, providing enhanced flexibility to the technician. The extremity is then measured to determine the length of the product to use. See FIG. 12. The medical bandaging material 10 is then dispensed from the foil sleeve 15 and cut to length. It is important to immediately reseal the sleeve 15 to prevent moisture intrusion which can harden the remaining material. See FIG. 13.

The liner sheet 12 may be removed, or may be left on the substrate. Any custom cuts should now be made in the medical bandaging material 10, before application of water. One side of the substrate 11 is wetted from a water bottle or by holding the medical bandaging material 10 under a faucet. In either case, a one-inch bead of water should be made to flow generally down the center of the medical bandaging material 10 using cool water (75–85° F.; 24–30° C.). Hot water will increase exotherm during the curing process and thus possibly discomfort the patient.

The medical bandaging material 10 is then folded and folded and squeezed to remove excess water. A towel should not be used. This is a distinct difference in technique from the preparation procedure for applicant's Orthoglass product. The medical bandaging material 10 is then formed into its original shape and smoothed to remove any wrinkles or creases. The medical bandaging material 10 is then immediately, while still flexible, applied over the previously-applied padding onto the injured extremity, being careful to conform the medical bandaging material 10 closely to the extremity and insure that no creases remain. The extremity is then wrapped with an elastic bandage 60 to maintain the conformity for at least 2–4 minutes, or until the medical bandaging material 10 has hardened.

Alternatively, the padding 50 can be formed to the substrate 10 before application to the injured extremity, in which can application proceeds as with applicant's Orthoglass product. Different thicknesses or single or multiple layers of padding can be used, as described above.

Use of the medical bandaging material 10 according to the invention is initially less expensive due to the absence of the padding layer. Moreover, the medical bandaging material 10 itself can be replaced if needed during treatment of the injury while reusing the padding, thus achieving further savings.

A medical bandaging product and material formed of a moisture-curable plastic material, a method for constructing such an improved medical bandage, and a method of constructing and applying an improved bandaging product is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A method of utilizing a medical bandaging product, comprising the steps of:
   (a) providing an elongate sleeve and an unpadded elongate medical bandage material consisting of an unpadded substrate and a reactive system enclosed within a very thin, protective liner sheet of no more than 1 mm in thickness, said protective liner sheet being adapted for permitting removal from the substrate of a subsequently-applied padding layer;
   (b) impregnating into or coating onto said substrate said reactive system which remains stable when maintained in substantially moisture-free conditions and hardens upon exposure to sufficient moisture to form a rigid, self-supporting structure;
   (c) positioning said elongate medical bandage material within said elongate sleeve;
   (a) sealing said sleeve to prevent entry of moisture until use;
   (f) removing the medical bandage material from the sleeve immediately prior to use;
   (g) wetting the substrate to activate the reactive system;
   (h) interposing a padding between the substrate and the patient; and
   (i) applying the substrate and interposed padding to the patient.

2. A method according to claim 1, wherein the step of interposing the padding between the patient and the substrate includes the step of applying the padding to the patient before the substrate is applied to the patient.

3. A method according to claim 1, wherein the step of interposing the padding between the patient and the substrate includes the step of applying the padding to the substrate before application to the patient.

4. A method according to claim 1, and including the step of overwrapping the padding and substrate with an elastic bandage to maintain the padding and substrate in close conformity with the patient during curing of the moisture-curable resin.

5. A medical bandaging product in roll form for being dispensed in predetermined lengths suitable for a given medical use, and comprising:
   a) an elongate sleeve formed of moisture-impervious material and sealable to prevent entry of moisture;
   (b) an elongate medical bandage material substantially the same length as the sleeve and positioned in said sleeve in a single length along the length of the sleeve and sealed therein against entry of moisture until use, said medical bandage material consisting of:
      (i) an substrate of a plurality of overlaid layers of unpadded woven or knitted fabric;
      (ii) a reactive system impregnated into or coated onto said substrate, said system remaining stable when maintained in substantially moisture-free conditions and hardening upon exposure to sufficient moisture to form a rigid, self supporting structure; and
      (iii) a very thin, protective liner sheet of no more than 1 mm in thickness enclosing said substrate along its length and forming a slick, low-friction contact surface for contact with the sleeve during storage, for preventing sticking between the substrate and an overlying padding layer interposed between the medical bandaging material and the skin of a patient, and adapted for permitting removal from the substrate of a subsequently-applied padding layer;
   (c) resealing means for resealing said sleeve against entry of moisture after a predetermined length of said bandaging product has been dispensed for use to prevent hardening of said substrate remaining in said sleeve.

6. A medical bandaging product according to claim 5, and including a tape extending along one edge of the liner sheet for adhering opposing side edges of the liner sheet to each other in surrounding relation to the substrate.

7. A medical bandaging product according to claim 5, wherein said liner sheet is 0.34 mm thick.

8. A medical bandaging product according to claim 7, wherein the liner sheet comprises a nonwoven material constructed of continuous filament fibers.

* * * * *